United States Patent [19]

Van der Knaap

[11] Patent Number: Plant 6,296

[45] Date of Patent: Sep. 20, 1988

[54] KALANCHOE PLANT NAMED KILIMANJARO

[75] Inventor: Jacques C. M. Van der Knaap, De Lier, Netherlands

[73] Assignee: Fides Beheer B.V., Del. Lier; Netherlands

[21] Appl. No.: 914,492

[22] Filed: Oct. 2, 1986

[51] Int. Cl.[4] ..... H01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Kilimanjaro, characterized by its rose flower color, strong growth habit, free branching, floriferous habit, average eleven week response, and its adaptability to production in 10–12 cm pots.

1 Drawing Sheet

The present invention relates to a new and distinct cultivar of Kalanchoe plant, botanically known as *Kalanchoe blossfeldiana,* and referred to by the cultivar name Kilimanjaro.

Kilimanjaro was originated from a cross made in a controlled breeding program in De Lier, The Netherlands. The female, or seed parent was a cultivar designated Etna (plant patent applied for). The male, or pollen parent was a cultivar designated Pluto, a commercially known but unpatented cultivar.

Kilimanjaro was discovered and selected by me as a flowering plant within the progeny of the stated cross in a controlled environment in De Lier, The Netherlands. Asexual reproduction of the new cultivar by shoot cuttings, as performed by me at De Lier, The Netherlands, has demonstrated that the combination of characteristics as herein disclosed for the new cultivar are firmly fixed and are retained through successive generations of asexual reproduction.

Kilimanjaro has not been observed under all possible environmental conditions. The phenotype may vary significantly with variations in environment such as temperature, light intensity and day length. The following observations, measurements and values describe the new cultivar as grown in De Lier, The Netherlands, under greenhouse conditions which closely approximate those generally used in commercial practice.

The following traits have been repeatedly observed and are determined to be basic characteristics of Kilimanjaro, which in combination distinguish this Kalanchoe as a new and distinct cultivar:

1. Rose flower color.
2. Strong growth.
3. Freely branching, with shoots formed at every node.
4. Suitable for production in 10–12 cm pots.
5. Highly floriferous, with numerous flowers formed at every shoot.
6. To reduce peduncle elongation after flower initiation, plants must be treated with Alar/B 9 or Bonzi.

The new cultivar is most similar to Sensation, disclosed in U.S. Plant Pat. No. 4,727. Kilimanjaro is distinguished from Sensation by its flower color, which is a lighter rose pink, growth habit, and leaf characteristics.

The accompanying photographic drawing shows a typical specimen plant of the new cultivar. The colors appearing in the photograph are as true as possible with color illustrations of this type.

In the following description, color references are made to the Royal Horticultural Society Colour Chart (R.H.S.), except where general colors of ordinary significance are referred to. Color values are taken under natural light conditions at approximately 10:00 a.m. in De Lier, The Netherlands.

Botanical classification: *Kalanchoe blossfeldiana,* cv. Kilimanjaro.

Parentage:

*Male parent.*—Pluto.

*Female parent.*—Etna.

Propagation: The new cultivar holds its distinguishing characteristics through successive propagations by leaf cuttings and by division of shoots.

(A) *Type cutting.*—Shoot cutting.

(B) *Time to root.*—Summer: 12 days at 21°; winter, 17 days.

(C) *Rooting habit.*—Large, thick roots.

Plant description:

(A) *Form.*—Upright, medium sized; growing and scheduling practices can produce medium or larger sized plants.

(B) *Habit of growth.*—Good growth rate for this type of plant; shoots are normally formed at every node.

(C) *Foliage description.*—Leaves simple, opposite, generally symmetrical. (1) Size: Average, full grown leaf of a flowering plant of Kilimanjaro when grown in a 10 cm pot is 115 mm long and 75 mm wide. (2) Shape: Ovate, apex obtuse, base truncate. (3) Texture: Glabrous, coriaceous, succulent. (4) Margin: Slightly crenate. (5) Color: Young foliage top side 147B, under side 147C. Mature foliage top side 147A, under side 147B.

Flowering description:

(A) *Flowering habit.*—Inflorescence of each shoot is formed by dichotomous branching, starting with opening of terminal flower at main axis, followed by terminal flowers of the side branches of the inflorescence. Opening of new buds will continue for 9 weeks or more. Individual flowers last 3 weeks or more after opening.

(B) *Natural flowering season.*—November. Flowering time under controlled day length at 25° C. in summer is 10 weeks; in winter at 20° C., 11 weeks. Flowering time depends on temperature, light intensity and other growing conditions.

(C) *Flower buds.*—Oblong, developing to tubular as petals mature sheathed with four green sepals; corolla at maturity about 12 mm. (1) 15 mm. (2) Shape: Oblong. (3) Rate of opening: Normal.

(D) *Flowers borne.*—Compound dichasial cyme on fairly strong peduncles. Peduncle length up to 5 mm long, depending on growing conditions and B/9/Alar applications.

(E) *Quantity of flowers.*—Very floriferous with new buds continuing to develop.

(F) *Petals.*—(1) Shape: Nearly round, apex cuspidate. (2) Color: Top side when opening, 55A, fading to 55B; under side, 56D. (3) Number and size of petals: Four (4), united in corolla; petals 6 mm in diameter, total flower diameter 12 mm.

(G) *Reproductive organs.*—(1) Stamens: Eight (8) in number. (a) Anther shape: Flat, elliptical. (b) Filament color: Yellow. (c) Pollen color; Yellow. (2) Pistels: (a) Stigma shape: Flat, crystalline. (b) Style color: Light green-yellow. (c) Ovaries: 4-celled, 6 mm long, light green.

Disease resistance: No known Kalanchoe diseases observed to date.

I claim:

1. A new and distinct cultivar of Kalanchoe plant named Kilimanjaro, as described and illustrated, and particularly characterized by its rose flower color, strong growth habit, free branching, floriferous habit, average eleven week response, and adaptability to production in 10–12 cm pots.

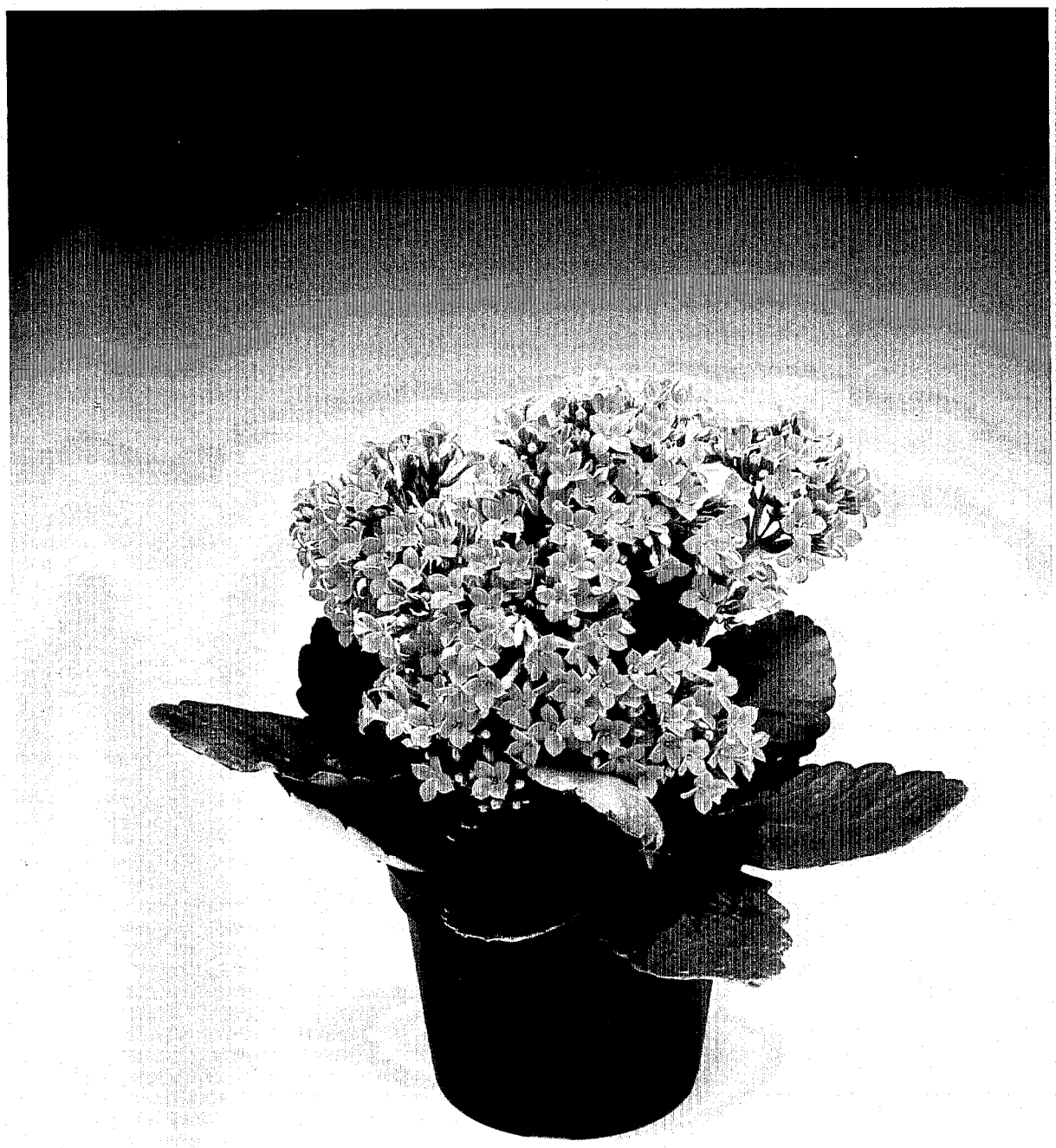

* * * * *